United States Patent [19]
McNamara et al.

[11] Patent Number: 4,925,833
[45] Date of Patent: May 15, 1990

[54] USE OF TETRACYCLINE TO ENHANCE BONE PROTEIN SYNTHESIS AND/OR TREATMENT OF OSTEOPOROSIS

[75] Inventors: Thomas F. McNamara, Port Jefferson; Lorne M. Golub, Smithtown; Nungavaram S. Ramamurthy, Smithtown, all of N.Y.

[73] Assignee: The Research Foundation of State University of New York, Albany, N.Y.

[21] Appl. No.: 946,726

[22] Filed: Dec. 29, 1986

Related U.S. Application Data

[63] Continuation-in-part of Ser. No. 699,048, Feb. 7, 1985, Pat. No. 4,704,383, which is a continuation-in-part of Ser. No. 566,517, Dec. 29, 1983, Pat. No. 4,666,897.

[51] Int. Cl.$^5$ .............................................. A61K 31/65
[52] U.S. Cl. ..................................................... 514/152
[58] Field of Search ......................................... 514/152

[56] References Cited

U.S. PATENT DOCUMENTS 2,895,880  7/1959  Rosenthal ........................... 514/723
3,304,227  2/1967  Loveless ............................. 514/152
4,371,465  1/1983  McGregor .......................... 530/330

OTHER PUBLICATIONS

Chemical Abstracts, 100:96203a (1983).

Primary Examiner—Leonard Schenkman
Attorney, Agent, or Firm—Cooper & Dunham

[57] ABSTRACT

Tetracyclines, antibacterial and non-antibacterial tetracyclines, have been found to be useful in the treatment of osteoporosis in humans by administering to the human suffering from osteoporosis an effective amount of a tetracycline to enhance bone protein synthesis. Tetracyclines which have been found to be effective in the treatment of osteoporosis in humans include minocycline, doxycycline and dedimethylaminotetracyline.

19 Claims, No Drawings

USE OF TETRACYCLINE TO ENHANCE BONE PROTEIN SYNTHESIS AND/OR TREATMENT OF OSTEOPOROSIS

This application is a continuation-in-part application of copending, coassigned patent application Ser. No. 699,048 filed Feb. 7, 1985, now U.S. Pat. No. 4,704,383 which, in turn, is a continuation-in-part of copending, coassigned patent application Ser. No. 566,517 filed Dec. 29, 1983, now U.S. Pat. No. 4,666,897.

The disclosures of the above-identified applications are herein incorporated and made part of this disclosure.

BACKGROUND OF THE INVENTION

In pending U.S. patent application Ser. No. 566,517, now U.S. Pat. No. 4,666,897, it is disclosed that tetracyclines, such as the antibiotic tetracyclines, e.g tetracycline, are useful as anti-collagenolytic agents or as inhibitors of collagenase. These tetracyclines and compositions containing the same are disclosed therein as being useful in the treatment of periodontal diseases, corneal ulcers, rheumatoid arthritis and the like characterized by excessive collagen destruction.

In pending U.S. patent application Ser. No. 699,048, now U.S. Pat. No. 4,704,383, it is disclosed that the non-antibiotic or non-antibacterial tetracyclines also possess anti-collagenolytic properties and are useful as inhibitors of collagenase. Additionally, these non-antibiotic or non-antibacterial tetracyclines have also been found to be useful in the treatment of periodontal diseases, corneal ulcers, bone deficiency disorders due to excess collagenase production or excessivde collagen destruction, rheumatoid arthristis and the like. A particularly useful non-antibiotic tetracycline in the practices of this invention is the tetracycline dedimethylaminotetracycline.

Tetracyclines are useful as broad spectrum antibiotics because they have the ability to inhibit protein synthesis in a wide variety of bacteria. As disclosed in the above-identified pending patent applications, it has also been discovered that tetracyclines, antibiotic tetracyclines and non-antibiotic tetracyclines, have the ability to inhibit collagen-destructive enzymes, such as collagenase, responsible for the breakdown of connective tissue in a number of diseases, such as periodontal disease, corneal ulcers and rheumatoid arthritis.

SUMMARY OF THE INVENTION

It has now been discovered that inhibitors of collagen-destructive enzymes, such as collagenase, are useful in the treatment of mammals, such as humans, to prevent the development of osteoporosis and/or to stimulate bone protein synthesis. In the practices of this invention an effective amount of a physiologically acceptable collagenase inhibitor is systemically administered to the mammal or human to bring about the stimulation of bone protein synthesis or to treat bone deficiency disease or osteoporosis. The amount of the inhibitor administered to the mammal or human can be at a therapeutic level, i.e. substantially the same dosage as would be employed in the treatment of bacterial infections and the like, or at a reduced, subtherapeutic level, in the range about 5–60% of the therapeutic dosage. The amount administered in accordance with the practices of this invention would be effective to inhibit the collagen-destructive enzymes, such as collagenase, in the mammal, e.g. subject to which the inhibitor is administered.

More particularly, it has been discovered that tetracyclines, antibacterial and non-antibacterial tetracyclines, which are inhibitors of collagenase, enhance or stimulate bone protein synthesis and have been found to be useful in the treatment of osteoporosis in humans. In the light of the discovery of this invention that tetracyclines stimulate and enhance bone protein synthesis, tetracyclines have been found to be useful in the treatment of osteoporosis.

DETAILED DESCRIPTION OF THE INVENTION

The following disclosures or examples are illustrative of the practices of this invention.

EXAMPLE NO. 1

In this experiment 4 groups of adult male rats were set up, viz. a group of normal rats which served as controls, a group of rats that were rendered diabetic by streptozotocin administration and two additional groups of diabetic rats, one of which was administered by oral intubation 20 mg per day of a chemically modified non-antibiotic tetracycline (CMT), and the other of which was orally administered 5 mg per day of minocycline, a semi-synthetic commercially available antibiotic tetracycline. Each of the 4 groups of rats contained 4 rats each. Three weeks after beginning the experiment, but 2 hours before sacrifice, each rat was injected with 1 mCi of $H^3$-proline to radioactively label the newly synthesized protein in the skeletal and other tissues. After the rats were killed, the long bones were removed, cleaned free of soft tissue, the mid-shaft of the cleaned bone collected and hydrolyzed in 6N HCl (24 h, 105° C.), and an aliquot measured in a liquid scintillation spectrometer after evaporating the acid. The data on bone protein synthesis is shown in Table I.

TABLE I

| The administration of minocycline or chemically-modified non-antibiotic tetracycline (CMT) to diabetic rats: effect on bone protein synthesis in vivo | |
|---|---|
| Experimental Group | Bone protein synthesis (DPM $H^3$-Pro/mg bone tissue) |
| Controls | 886 ± 155 |
| Diabetics (D) | 588 ± 89 |
| D + minocycline | 852 ± 145 |
| D + CMT | 828 ± 248 |

Inducing diabetes in the rat suppressed protein synthesis in the skeletal tissue; after months of this metabolic dysfunction in the bones, they developed physically and chemically-detectable bone-deficiency disease. When either of the two tetracyclines was orally administered to the diabetics, bone protein synthesis was increased to essentially normal values, and this metabolic alteration was associated with the prevention of the devleopment of osteoporosis.

EXAMPLE NO. 2

In this experiment 3 groups of animals were established: a group of non-diabetic controls, a group of untreated diabetics, and a group of diabetic rats that were administered, by the oral route, 1.5 mg doxycycline, an antibiotic tetracycline, per day for the entire 3½ month experimental period. After 3.5 months, the rats were killed, the bones (femur and tibia) were removed, defleshed, and radiographs taken. Physical and biochemical parameters were also measured. Other bones (mandible) were processed for light microscopy. Diabetes significantly reduced the dry weight, density, ash, matrix, calcium and hydroxyproline contents of the skeletal tissue (the unchanged Ca/Hyp ratio indicated the bone was normally calcified even though osteopenic). Long-term doxycycline therapy retarded the loss of organic and inorganic bone constituents in the diabetics even though the severity of hyperglycemia was unaffected. Radiographic changes were consistent with the above findings. In short-term studies, treatment of diabetic rats with a different tetracycline (minocycline) showed a similar pattern of results. Tetracycline therapy in rats retarded osteoporotic changes in bone induced by diabetes.

It was observed that untreated diabetic rats developed bone deficiency disease, or osteoporosis, based on physical, radiologic, chemical and histologic assessments. However, the tetracycline, doxycycline, therapy prevented the development of diabetes-induced osteoporosis even though the drug had no effect on the severity of the diabetic state, presumably because the drug increased the depressed protein synthesis in the skeletal tissues.

EXAMPLE NO. 3

TABLE II

Effect of CMT Administration (20 mg per day) on Urinary Calcium Excretion in Streptozotocin-Diabetic Rats

| Experimental Group | Number of Rats per Group | μg Ca in urine per 24 h* |
|---|---|---|
| Control | 4 | 33 ± 5 |
| Diabetes | 4 | 691 ± 35 |
| Diabetes + CMT | 4 | 398 ± 33 |

*Each value represents the mean ± S.E.M. of 12 values: a 24 h determination was made, for each rat (n = 4 per group), on days 18, 19 and 20 after inducing diabetes.

The results shown above in Table II summarizes the reduction in calcium excretion in the diabetic animals treated with CMT as compared with the untreated diabetic animals. Diabetes dramatically increases the urinary excretion of calcium compared with control values and an elevated urinary excretion of calcium is associated with the development of osteoporosis. Administration of CMT to the diabetic animals reduced the pathologically excessive excretion of calcium by 42%; this is biochemical evidence of the amelioration of the condition resulting from the administration of CMT.

EXAMPLE NO. 4

Tetracycline can inhibit tissue degradation by anti-collagenase action and has reduced pathological bone resorption through this mechanism (Golub et al. 1983, 84). A study was undertaken to evaluate whether tetracycline could have any discernible effect upon morphologic characteristics of bone undergoing normal remodeling. Four squirrel monkeys received a daily dose of tetracycline at 100 mg/kg/day given by oral intubation in 3 equal doses. After 17 days of tetracycline administration, the animals were sacrificed and the jaws processed for histologic sectioning. Bucco-lingual sections were prepared from bicuspid and cuspid teeth. A defined coronal buccal alveolar bone region was analyzed histologically and histometrically using step-serial sections. Corresponding regions were analyzed from bicuspids and cuspids from 4 animals which had not received tetracycline administration. Morphologic characteristics of the bone were analyzed using a Bioquant computerized digitization system, and comparisons made between the groups. Within the defined region, the total area of alveolar bone and the number of marrow spaces, did not differ between the two groups. However, the area of the narrow spaces was significantly less in tetracycline-receiving animals. The marrow spaces occupied $0.5 \pm 0.09(SE)\%$ of the bone in tetracycline-receiving animals, in contrast to the $7.9 \pm 1.2(SE)\%$ ($t = 3.49$, $p < 0.01$) present in control animals. In the tetracycline-receiving animals, the marrow spaces appeared to be lined by new bone, as were the periodontal ligament surfaces of the alveolar bone. The increased bone density may have been due to inhibition of resorption without affecting the deposition phase of bone remodeling.

Although in the practices of this invention many compounds, particularly physiologically acceptable collagenase inhibitors, are useful, it is preferred to employ a tetracycline antibiotic or non-antibiotic. Tetracyclines, broadly, can be characterized as containing four fused carbcyclic groups. This arrangement appears to be characteristic of compounds which are collagenase inhibitors and which are also useful in the practices of this invention. Related compounds, compounds which are related as analogs or homologs of tetracycline, are also useful as well as compounds which are characterized as having three fused carbocyclic groups. Suitable such compounds are disclosed herein and include 7-chlorotetracycline, 5-hydroxytetracycline, 6-demethyl-7-chlorotetracycline, 6-demethyl-6-deoxy-5-hydroxy-6-methylenetetracycline, 6-alpha-benzylthiomethylenetetracycline, a nitrile analog of tetracycline, a mono-N-alkylated amide of tetracycline, 6-fluorodemethyltetracycline, 11-alpha-chlorotetracycline, 2-acetyl-8-hydroxy-1-tetracycline and 6-demethyl-6-deoxytetracycline.

As mentioned hereinabove, the compounds employed in the practices of this invention are employed in an effective amount for the treatment of osteoporosis, such as an amount effective to enhance the synthesis of bone protein and/or correct or treat any deficiency disease. The amount employed depends to some extent upon the body weight of the mammal or human being treated. With respect to humans, the amount employed, particularly in the case of compounds which are collagenase inhibitors and/or characterized as being a tetracycline, on a daily dosage, it is usually less than about 400 milligrams and usually below about 200 milligrams. A suitable daily dosage for a human would be in the range 10 milligrams to about 50 milligrams for the treatment of osteoporosis or other bone deficiency disease and for the enhancement of the synthesis of bone protein.

As will be apparent to those skilled in the art in the light of the foregoing disclosure, many alterations, substitutions and modifications are possible in the practices of this invention without departing from the spirit or scope thereof.

What is claimed is:

1. A method of treating osteoporosis by enhancing bone protein synthesis in a human which comprises administering to the human an effective amount of a tetracycline.

2. A method in accordance with claim 1 wherein said tetracycline is an antibacterial tetracycline.

3. A method in accordance with claim 1 wherein said tetracycline is non-antibacterial tetracycline.

4. A method in accordance with claim 1 wherein said tetracycline is minocycline.

5. A method in accordance with claim 1 wherein said tetracycline is doxycycline.

6. A method in accordance with claim 1 wherein said tetracycline is 7-chlorotetracycline.

7. A method in accordance with claim 1 wherein said tetracycline is 5-hydroxytetracycline.

8. A method in accordance with claim 1 wherein said tetracycline is 6-demethyl-7-chlorotetracycline.

9. A method in accordance with claim 1 wherein said tetracycline is 6-demethyl-6-deoxy-5-hydroxy-6-methylenetetracycline.

10. A method in accordance with claim 1 wherein said tetracycline is dedimethylaminotetracycline.

11. A method in accordance with claim 1 wherein said tetracycline is 6-alpha-benzylthiomethylenetetracycline.

12. A method in accordance with claim 1 wherein said tetracycline is a nitrile analog of tetracycline.

13. A method in accordance with claim 1 wherein said tetracycline is a mono-N-alkylated amide of tetracycline.

14. A method in accordance with claim 1 wherein said tetracycline is 6-fluorodemethyltetracycline.

15. A method in accordance with claim 1 wherein said tetracycline is 11-alpha-chlorotetracycline.

16. A method in accordance with claim 1 wherein said tetracycline is 2-acetyl-8-hydroxy-1-tetracycline.

17. A method in accordance with claim 1 wherein said tetracycline is 6-demethyl-6-deoxytetracycline.

18. A method in accordance with claim 1 wherein said tetracycline is administered systemically.

19. A method in accordance with claim 1 wherein said tetracycline is administered orally.

* * * * *

UNITED STATES PATENT AND TRADEMARK OFFICE
CERTIFICATE OF CORRECTION

PATENT NO. : 4,925,833
DATED : May 15, 1990
INVENTOR(S) : LORNE M. GOLUB ET AL

It is certified that error appears in the above-identified patent and that said Letters Patent is hereby corrected as shown below:

TITLE PAGE: The order of inventorship should correctly read:

--LORNE M. GOLUB, THOMAS F. McNAMARA and NUNGAVARAM S. RAMAMURTHY--

Item [19] should read "Golub et al".

Signed and Sealed this

Seventeenth Day of December, 1991

Attest:

HARRY F. MANBECK, JR.

*Attesting Officer*     *Commissioner of Patents and Trademarks*